US00PP08136P

United States Patent [19]

Holtkamp, Sr.

[11] Patent Number: Plant 8,136

[45] Date of Patent: Feb. 9, 1993

[54] AFRICAN VIOLET PLANT NAMED BERLIN

[76] Inventor: Reinhold Holtkamp, Sr., Blumenstrasse 28, D4242 Rees-Haffen, Fed. Rep. of Germany

[21] Appl. No.: 736,217

[22] Filed: Jul. 26, 1991

[51] Int. Cl.[5] ..... A01H 5/00

[52] U.S. Cl. ..... Plt./69.2

[58] Field of Search ..... Plt./69.1, 69.2

*Primary Examiner*—James R. Feyrer

*Attorney, Agent, or Firm*—Foley & Lardner

[57] ABSTRACT

A new and distinct cultivar of African violet named Berlin characterized by its extra large growth habit (30–40 cm in diameter); blue, star-shaped, semi-double flowers with frilled white edges; strong stems which curve toward the center to form a bouquet above the leaves; profuse flowering; large, medium green, wavy leaves; flowering 12–13 weeks after planting of unrooted shoot, and by its long lasting and non-dropping flowers.

1 Drawing Sheet

The present invention comprises a new and distinct cultivar of African violet plant, botanically known as *Saintpaulia ionantha*, and hereinafter referred to by the cultivar name Berlin.

The new cultivar was referred to during the breeding and selection process by the designation 905/50 bl.si.ra. and is a product of a planned breeding program. The cultivar was originated from a cross made by me in the controlled breeding program in Haffen, Federal Republic of Germany. The female, or seed parent, was a cultivar designated Arizona/6/III. The male, or pollen parent, was a cultivar designated 282 Molokai.

Berlin was discovered and selected by me as a flowering plant within the progeny of the stated cross in a controlled environment in Haffen, West Germany. Asexual reproduction of the new cultivar by leaf cuttings, as performed by me at Haffen, West Germany, has demonstrated that the combination of characteristics as herein disclosed for the new cultivar are firmly fixed and retained through successive generations of asexual reproduction.

Berlin has not been observed under all possible environmental conditions. The phenotype may vary significantly with variations in environment such as temperature, light intensity and day length. The following observations, measurements and values describe the new cultivar as grown in a 15 cm pot in Haffen, West Germany and Nashville, Tenn. under greenhouse conditions which closely approximate those generally used in commercial practice.

The following traits have been repeatedly observed and are determined to be basic characteristics of Berlin, wich in combination distinguish this African violet as a new and distinct cultivar:

1) A single crown will grow as large as 30–40 cm in diameter.

2) Blue, star-shaped, semi-double flowers with frilled white edges.

3) Strong, wirelike and upright flower stems curving toward the center.

4) First flash of flowers forms a bouquet above the leaves.

5) Profuse flowering.

6) Each plant carries 8–11 and more upright flower stems each of which carries 8–10 and more flowers.

7) Long lasting, non-dropping flowers.

8) Plant saleable 12 to 13 weeks after planting of unrooted shoot.

9) Seed capsules push slightly through.

10) Large medium green, wavy leaves.

11) After maturity the flowers dry off, and remain on the peduncle without becoming infected by botrytis.

The accompanying color photographic drawing shows a typical specimen plant of the new cultivar grown in a 15 cm pot. The colors appearing in the photograph are as true as possible with color illustrations of this type.

In the following description, color references are made to The Royal Horticultural Society Color Chart (R.H.S.), except where general colors of ordinary significance are referred to. Color values were taken under natural sunlight conditions at approximately 12 p.m. in Nashville, Tenn.

Botanical classification: *Saintpaulia ionantha*, Ramat., c.v. Berlin.

Parentage:

*Male parent.*—282 Molokai.

*Female parent.*—Arizona/6/III.

Propagation: The new cultivar holds its distinguishing characteristics through successive propagations by leaf cuttings.

Plant: From 10 cm to 13 cm tall when grown in pots, and 35–40 cm in diameter when fully grown.

*Leaves.*—General form: Oval. Diameter: 75–90 mm wide and 85–90 mm long. Texture: Velvety. Aspect: Wavy, serrated, hairy, shiny. Veins: Upperside: visible; underside: well pronounced, light green, shiny. Color (upperside): Yellow-green group 147 A. Color (underside): Greyed-green group 194 C with touches of Greyed-Purple Group 186 C to D. Young leaves are Greyed-Purple Group 186 B to C. Petiole: Strong, green with brownish touch, hairy.

*Flowers.*—Buds: Size: 8–10 mm just before opening. Shape: Bell-shaped. Color: Green with bluish touch. Sepals: Five (5). Color: Reddish brown. Calyx: Shape: Funnel-shaped. Aspect: Spear-shaped, hairy. Peduncle: Character: Strong upright, hairy. Color: Brownish green. Individual flowers: Size: 45–48 mm Shape: Star-shaped, semi-double with frilled edges. Color (upperside): Violet-blue group 93 B to C. Under cooler temperatures and more intensive lighting, the blue tends to intensity. Color (underside): Violet-blue group 89 D. Borne: Each flower stem carries 8–10 and more flowers on strong, upright peduncles that are free standing above the leaves, thereby forming a compact bouquet. Flowering habit: Flowers 12–13 weeks after planting an unrooted plantlet.

*Reproductive organs.*—Stamens: Five (5 ). Anthers: 5 composed of 10 anther cells, seed capsule pushes slightly through. Filaments: Yellowish green, 4–5 mm long. Styles: 6–7 mm long, purplish blue, base of ovary light green and hairy.

*Roots.*—Normally developed, white when young, turning slightly brownish when older.

Diease resistance: Up to date, Berlin has shown very good resistance to all major violet diseases.

General observations: Berlin is a very attractive cultivar due to its extra large growth habit. It is designed to be grown in a 15 cm pot (instead of the regular 10 cm pot) and will grow as large as 35–40 cm in diameter. (The diameter can vary depending on how firmly the potting medium is compressed). A nice bouquet of flowers free standing above the leaves develops 12–13 weeks after planting an unrooted plantlet. Each of the 8–11 and more strong flower stems carries 8–10 and more star-shaped, semi-double blue flowers with frilled white edges. The anthers are usually covered up by several small petals in the center. The flowers are long-lasting and non-dropping. The bouquet is surrounded by large, medium green, wavy leaves.

I claim:

1. A new and distinct cultivar of African violet named Berlin, as described and illustrated, and particularly characterized by its extra large growth habit (30–40 cm in diameter); blue, star-shaped, semi-double flowers with frilled white edges; strong stems which curve toward the center to form a bouquest above the leaves; profuse flowering; large, medium green, wavy leaves; flowering 12–13 weeks after planting of unrooted shoot, and by its long lasting and non-dropping flowers.

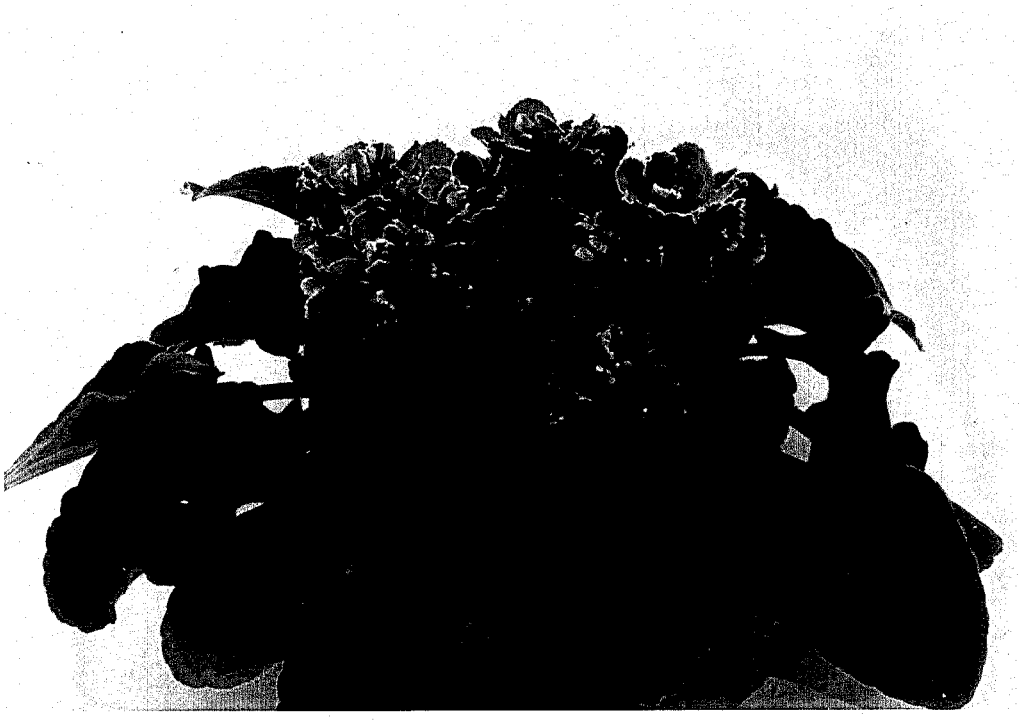

* * * * *